(12) United States Patent
Ueda et al.

(10) Patent No.: US 10,238,858 B2
(45) Date of Patent: Mar. 26, 2019

(54) CONNECTOR AND INFUSION SET

(71) Applicant: TERUMO KABUSHIKI KAISHA, Tokyo (JP)

(72) Inventors: Yasuhiro Ueda, Kofu (JP); Kazuya Akiyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 231 days.

(21) Appl. No.: 15/274,630

(22) Filed: Sep. 23, 2016

(65) Prior Publication Data

US 2017/0007819 A1    Jan. 12, 2017

Related U.S. Application Data

(63) Continuation of application No. PCT/JP2015/001643, filed on Mar. 23, 2015.

(30) Foreign Application Priority Data

Mar. 26, 2014  (JP) ................. 2014-064302

(51) Int. Cl.
- *A61M 5/14* (2006.01)
- *A61M 39/26* (2006.01)
- *A61M 39/10* (2006.01)

(52) U.S. Cl.
CPC ............ *A61M 39/26* (2013.01); *A61M 39/10* (2013.01); *A61M 2039/1033* (2013.01); *A61M 2039/1072* (2013.01)

(58) Field of Classification Search
CPC ...... A61M 39/00; A61M 39/04; A61M 39/10; A61M 39/26; A61M 2039/1033; A61M 2039/1072

(Continued)

(56) References Cited

U.S. PATENT DOCUMENTS 5,785,693 A    7/1998  Haining
8,585,661 B2  11/2013  Okiyama
(Continued)

FOREIGN PATENT DOCUMENTS

DE    10 2012 205 490    10/2013
EP         2 810 685          12/2014
(Continued)

OTHER PUBLICATIONS

International Search Report issued in International Patent Application No. PCT/JP2015/001643 dated Jun. 16, 2015.
(Continued)

*Primary Examiner* — Jason Flick
(74) *Attorney, Agent, or Firm* — Foley & Lardner LLP

(57) ABSTRACT

A connector includes a housing including: an insertion section into which a male connector is insertable from an outside of the housing, and a flow path communicating with the insertion section; and an elastic valve body having a slit and configured to block the insertion section. An inner wall of the housing defining the flow path is integrally formed with a liquid barrier face. The housing is configured such that, when the male connector is inserted in the insertion section, the liquid barrier face faces a tip opening of the male connector in an insertion direction of the male connector such that liquid flowing out from the tip opening collides with the liquid barrier face.

14 Claims, 16 Drawing Sheets

(58) Field of Classification Search
USPC .......................................................... 604/256
See application file for complete search history.

(56) References Cited

U.S. PATENT DOCUMENTS

2004/0195538 A1    10/2004  Raines et al.
2006/0184140 A1*    8/2006  Okiyama ............ A61M 39/045
                                                            604/249

FOREIGN PATENT DOCUMENTS

| EP | 2 815 786 | 12/2014 |
| JP | H10-127778 A | 5/1998 |
| JP | 2010-148757 A | 7/2010 |
| JP | 2013-500128 A | 1/2013 |
| WO | WO-2005/004973 A | 1/2005 |
| WO | WO-2011/014265 A1 | 2/2011 |
| WO | WO-2011/060384 | 5/2011 |
| WO | WO-2012/133131 | 10/2012 |
| WO | WO-2014/009823 | 1/2014 |

OTHER PUBLICATIONS

Extended European Search Report issued in European Patent Application No. 15769218.7 dated Aug. 30, 2017.

* cited by examiner

CONNECTOR AND INFUSION SET

CROSS-REFERENCE TO RELATED APPLICATIONS

This application is a continuation application of and claims the benefit of priority from International Patent Application No. PCT/JP2015/001643, filed Mar. 23, 2015, which claims priority to Japanese Patent Application No. 2014-064302, filed on Mar. 26, 2014, the entireties of which are hereby incorporated by reference.

BACKGROUND

The present disclosure relates to a connector and an infusion set. In particular, the present disclosure relates to a connector that is capable of connecting thereto a male connector and an infusion set using the connector.

Conventionally, when infusion, blood transfusion, or artificial dialysis is performed, liquid is fed into the body using a medical tube. When another liquid such as liquid medicine is joined to the liquid inside the tube, a connector that is capable of liquid-tightly connecting a male connector such as a syringe and a luer taper member to the medical tube is used. A male connector such as a syringe and a luer taper member may be called a male luer, and a connector connected to the male luer may be called a female luer.

WO 2005/004973 discloses a mixture injection port as a connector in which one end of a channel tube is covered by a septum provided with a slit into which a tube member is inserted. The channel tube is provided with a circulating portion for circulating a fluid injected from the inserted tube member or a fluid flowing toward the tube member to the septum side and then guiding the fluid to the downstream side of the channel tube or a tip of the tube member.

SUMMARY

The mixture injection port disclosed in WO 2005/004973 has a configuration in which the circulating portion, which is a member different from the channel tube, is mounted inside the channel tube as a housing. Therefore, there is a problem that manufacturing process need to include a step of mounting the circulating portion inside the channel tube, resulting in difficult manufacturing of the mixture injection port.

In consideration of the above problem, certain embodiments of the present invention provide a connector and an infusion set capable of suppressing continuous stagnation of internal liquid with a simple configuration.

A connector of a first aspect of the present invention includes a housing defining an insertion section into which a male connector is inserted from the outside and a flow path communicating with the insertion section and an elastic valve body which has a slit and blocks the insertion section. An inner wall defining the flow path is integrally formed with a liquid barrier face which faces a tip opening of the male connector inserted in the insertion section in an insertion direction of the male connector and collides with liquid flowing out from the tip opening.

As an embodiment of the present invention, preferably, the housing includes a partition section dividing the flow path in a direction perpendicular to the insertion direction and the liquid barrier face includes an upstream face which is a face of the partition section on an upstream side of the insertion direction.

As an embodiment of the present invention, preferably, the partition section divides the flow path into a plurality of separated flow paths in the direction perpendicular to the insertion direction.

As an embodiment of the present invention, preferably, the upstream face is a plane extending in the direction perpendicular to the insertion direction.

As an embodiment of the present invention, preferably, the upstream face is an inclined face descending from the upstream side to the downstream side of the insertion direction.

As an embodiment of the present invention, preferably, the partition section has a substantially round-shaped outer shape when seen from the insertion direction.

As an embodiment of the present invention, preferably, the housing includes a projecting wall section projecting toward the inner side from the inner wall and the liquid barrier face includes an upstream face which is a face of the projecting wall section on the upstream side of the insertion direction.

As an embodiment of the present invention, preferably, a maximum width of the partition section interposed between the flow paths is smaller than an internal diameter of the housing defining an insertion opening that is one end of the insertion section when the housing is seen from the insertion direction.

As an embodiment of the present invention, preferably, the inner wall defining the flow path is integrally formed with a tip receiving face to receive a tip of the male connector and the liquid barrier face is positioned on the downstream side with respect to the tip receiving face in the insertion direction.

An infusion set as a second aspect of the present invention includes the above connector.

Certainly embodiments of the present invention allow for providing a connector and an infusion set capable of suppressing continuous stagnation of internal liquid with a simple configuration.

DETAILED DESCRIPTION

Hereinafter, an embodiment of a connector and an infusion set according to the present invention will be described with reference to FIGS. 1 to 17. Common members are denoted by identical symbols throughout the drawings.

Figure 1:
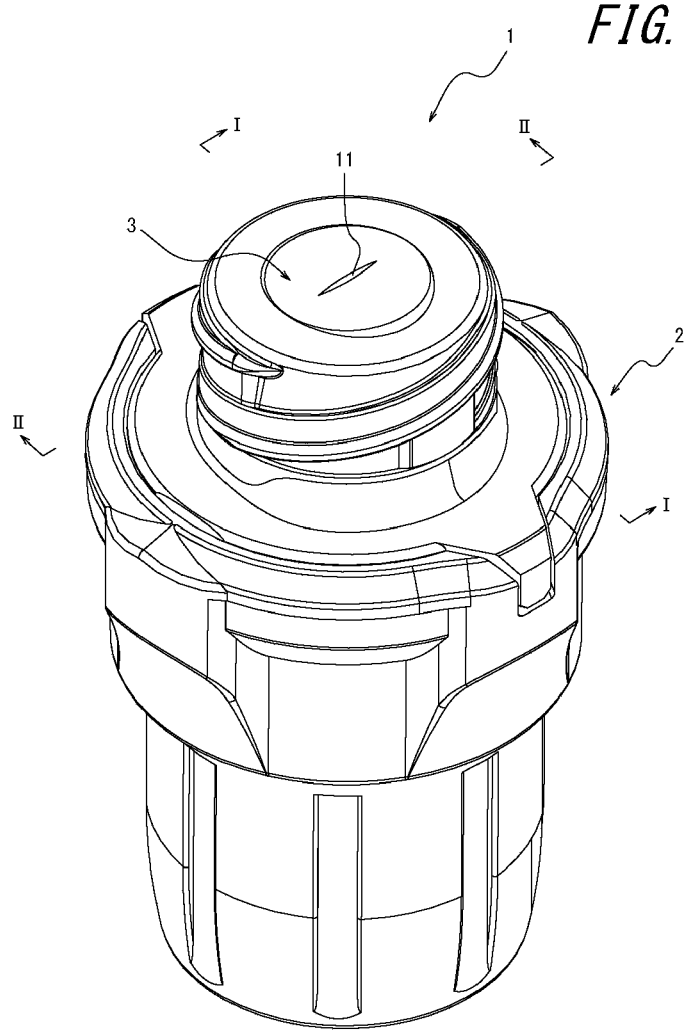
FIG. 1 is a perspective view illustrating a connector as an embodiment of the present invention.
Figure 2:
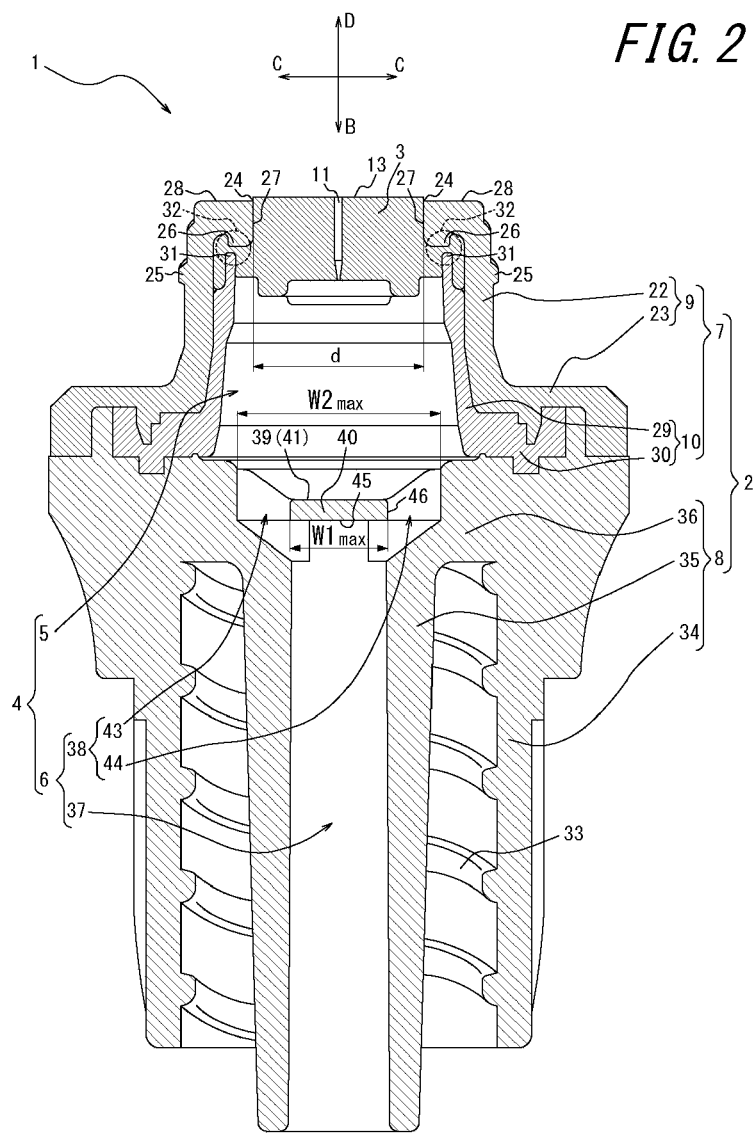
FIG. 2 is a cross-sectional view taken along line I-I of FIG. 1.
Figure 3:
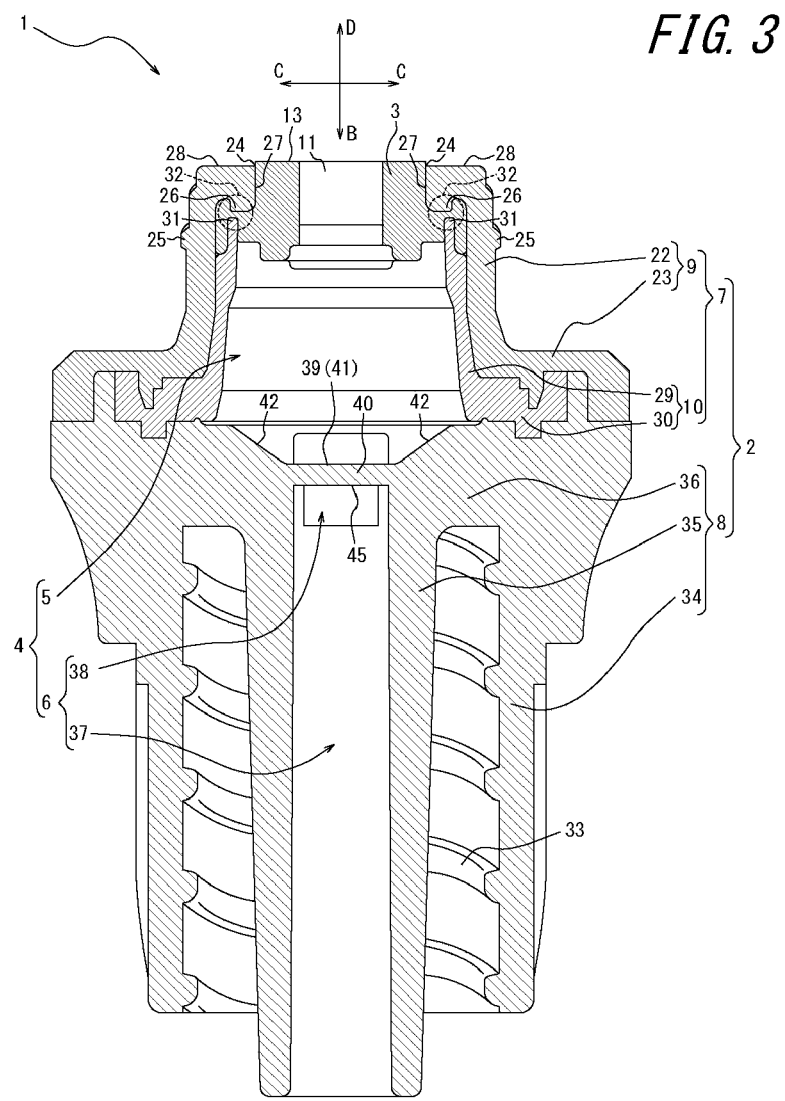
FIG. 3 is a cross-sectional view taken along line II-II of FIG. 1.

First, an embodiment of the connector according to the present invention will be described. FIG. 1 is a perspective view illustrating a connector 1 as the present embodiment. FIGS. 2 and 3 are cross-sectional views taken along line I-I and line II-II of FIG. 1, respectively.

As illustrated in FIGS. 1 to 3, the connector 1 includes a housing 2 and an elastic valve body 3 attached to the housing 2. Specifically, the connector 1 includes the housing 2 defining a hollow section 4 and the elastic valve body 3 positioned in the hollow section 4. The hollow section 4 includes an insertion section 5 into which a male connector 100 (see FIG. 9, etc.) is inserted from the outside and a flow path 6 communicating with the insertion section 5. The elastic valve body 3 blocks the insertion section 5. The "flow path communicating with the insertion section" includes not only a flow path directly connected to the insertion section but also a flow path connected to the insertion section via a separate space. The flow path 6 of the present embodiment is directly connected to the insertion section 5.

The housing 2 includes a cap 7 defining the insertion section 5 into which the male connector 100 (see FIG. 9, etc.) is inserted from the outside and a holder 8 defining the flow path 6 and supporting the cap 7.

The cap 7 includes a top face cap 9 and a bottom face cap 10. The elastic valve body 3 is compressed and clamped by the top face cap 9 and the bottom face cap 10 and thereby positioned and fixed in the hollow section 4, specifically, in the insertion section 5.

The holder 8 defines the flow path 6. The holder 8 is a member to support the top face cap 9 and the bottom face cap 10. In the present embodiment, both of the top face cap 9 and the bottom face cap 10 are in contact with and supported by the holder 8; however, the bottom face cap 10 may be held by the top face cap 9, thereby allowing only the top face cap 9 to be in contact with the holder 8 and to be supported by the holder 8. Conversely, the top face cap 9 may be held by the bottom face cap 10, thereby allowing only the bottom face cap 10 to be in contact with the holder 8 and to be supported by the holder 8.

In the present embodiment, the top face cap 9 and the bottom face cap 10 define the insertion section 5. The holder 8 further defines a part of the insertion section 5 and the flow path 6.

Examples of the materials of the holder 8 included in the housing 2 as well as the top face cap 9 and the bottom face cap 10 as the cap 7 include various resin materials such as: polyolefin such as polyethylene, polypropylene, and an ethylene-propylene copolymer; an ethylene-vinyl acetate copolymer (EVA); polyvinyl chloride; polyvinyliden chloride; polystyrene; polyamide; polyimide; polyamide-imide; polycarbonate; poly(4-methyl-1-pentene); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyetherketone (PEK); polyetheretherketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride and other fluororesins. A blend or a polymer alloy containing one or more kinds of the above resin materials may also be used. Alternatively, various glass materials, ceramic materials, or metal materials may be used.

The elastic valve body 3 has a slit 11 so that the elastic valve body 3 can elastically deform to open or close when the male connector 100 (see FIG. 9, etc.) is attached to or detached from the connector 1 and is arranged to block the insertion section 5 defined by the top face cap 9 and the bottom face cap 10 as the cap 7. Specifically, the elastic valve body 3 is clamped by a clamping section 32 formed by the top face cap 9 and the bottom face cap 10 and thereby positioned and fixed in the connector 1.

The elastic valve body 3 is molded and formed to be elastically deformable. Examples of the material of the elastic valve body 3 include: various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer. A mixture of one or two or more kinds of these materials may be used.

The hardness of the elastic valve body 3 is preferably 20 to 60° (A hardness). This allows for ensuring a moderate elastic force in the elastic valve body 3. Thus, elastic deformation (described later) can be generated in the elastic valve body 3.

Hereinafter, each member in the present embodiment will be described in detail.

[Elastic Valve Body 3]

Figure 4:
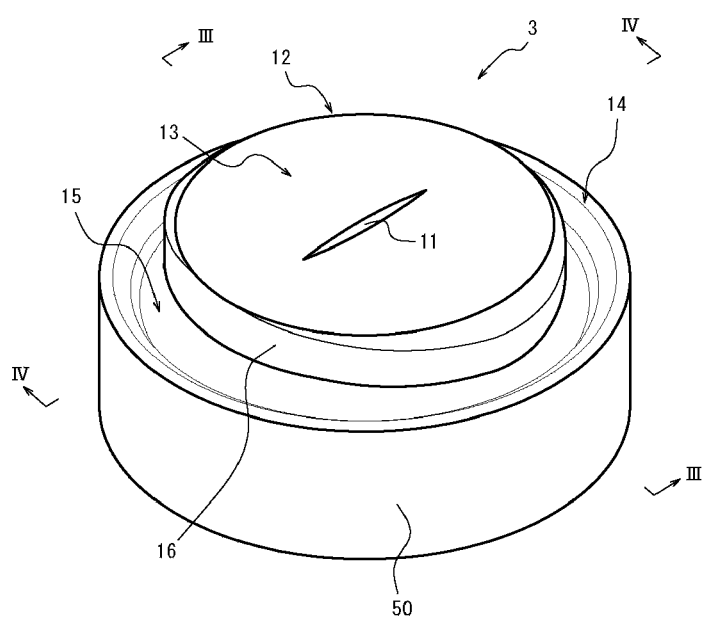
FIG. 4 is a perspective view of an elastic valve body alone.
Figure 5A:
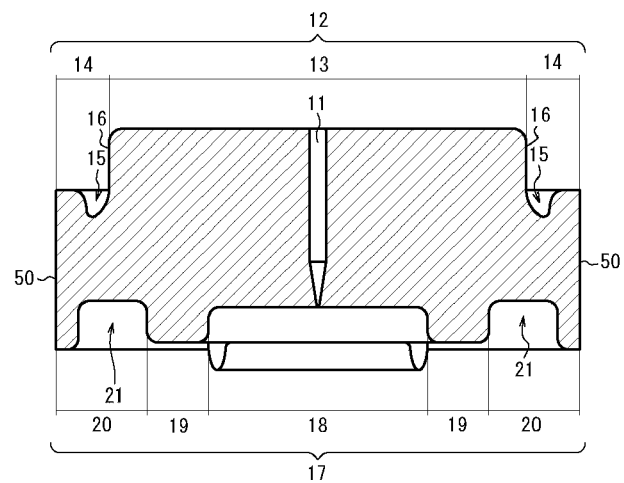
FIG. 5A is a cross-sectional view taken along line III-III of FIG. 4.
Figure 5B:
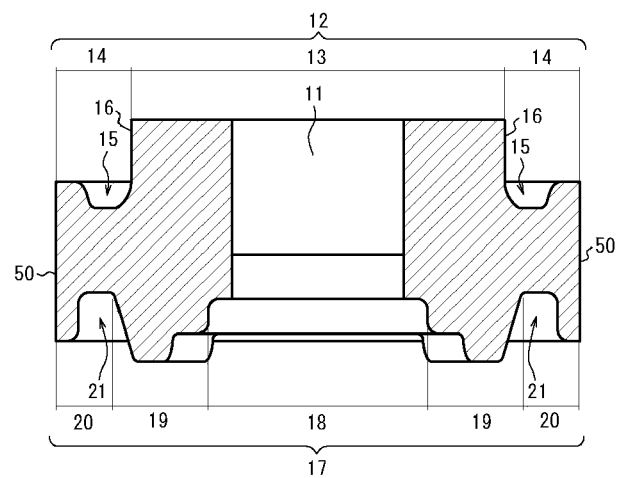
FIG. 5B is a cross-sectional view taken along line IV-IV of FIG. 4.

FIG. 4 is a perspective view of an elastic valve body 3 alone. FIGS. 5A and 5B are cross-sectional views taken along line III-III and line IV-IV of FIG. 4.

As illustrated in FIGS. 4 and 5, the elastic valve body 3 is a round and flat disc-like valve body having a disc-like outer shape. The top face 12 (upper face in FIGS. 5A and 5B) includes a planar top face central region 13 and a top face outer region 14 which is located on the outer side in the radial direction with respect to the top face central region 13.

The top face central region 13 has a shape projecting outward (upward in FIGS. 5A and 5B) with respect to the top face outer region 14. The straight slit 11 is formed in the center of the top face central region 13. The slit 11 is molded. The slit 11 does not penetrate the elastic valve body 3 up to a bottom face 17 when molded, and penetrates the elastic valve body 3 up to the bottom face 17 when, for example, the male connector 100 (see FIG. 9, etc.) is first inserted after the molding. A process of allowing the slit 11 to penetrate the elastic valve body 3 may be executed as a part of the manufacturing process after the molding is completed.

As illustrated in FIGS. 4 to 5B, a top face annular groove 15 is formed on the top face outer region 14 in a manner to surround the top face central region 13. A locking projection 26 (described later) (see FIGS. 2 and 3) of the top face cap 9 enters the top face annular groove 15 and compresses the elastic valve body 3 to constitute a part of the clamping section 32 (see FIGS. 2 and 3). In the top face annular groove 15 of the present embodiment, a groove wall adjacent to the top face central region 13 is formed in a circular arc shape in the sectional views of FIGS. 5A and 5B. Such a configuration enables a restoring performance of the elastic valve body 3 to be improved. In the present embodiment, although the top face annular groove 15 is formed at a position adjacent to the top face central region 13, that is, a side wall 16 of the top face central region 13 projecting outward in the sectional views of FIGS. 5A and 5B constitutes also the groove wall of the top face annular groove 15, the position or the shape of the top face annular groove 15 may be appropriately modified according to the position or the shape of the locking projection 26 of the top face cap 9.

The bottom face 17 of the elastic valve body 3, the bottom face 17 located opposite to the top face 12, includes a planar bottom face central region 18, a thick region 19 which is located on the outer side in the radial direction with respect to the bottom face central region 18, and a bottom face outer region 20 which is located on the outer side in the radial direction with respect to the thick region 19.

The slit 11 is not formed on the bottom face central region 18. However, as described above, for example, when the male connector 100 is first inserted, a part between a tip of the slit 11 formed on the top face 12 and the bottom face central region 18 is split, which allows the slit 11 to communicate with the top face central region 13 through to the bottom face central region 18.

The thick region 19 projects outward (downward in FIGS. 5A and 5B) with respect to the bottom face central region 18 and the bottom face outer region 20. In a configuration that is not provided with the thick region 19, when an excessive load is applied to the elastic valve body 3 during insertion or removal of the male connector 100 or when the male connector 100 is repeatedly attached and detached, longitudinal ends of the communicating slit 11, the longitudinal ends facing the bottom face 17, may disadvantageously be split. The thick region 19 reinforces the longitudinal ends and thereby enables suppressing occurrence of the above problem. In the present embodiment, when the elastic valve body 3 is viewed from the bottom face 17, the annular thick region 19 is formed in a manner to surround the slit 11 formed on the top face 12 and thickest at positions on the outer side in the longitudinal direction of the slit 11. Such a configuration allows for preventing the ends of the slit 11 from being split and to ensure both of excellent insertability of the male connector and maintenance of the elastic restoring force of the elastic valve body 3.

A bottom face annular groove 21 is formed on the bottom face outer region 20 in a manner to surround the thick region 19. A locking projection 31 (described later) of the bottom face cap 10 enters the bottom face annular groove 21 and compresses the elastic valve body 3 to constitute a part of the clamping section 32 (see FIGS. 2 and 3).

As illustrated in FIGS. 4 to 5B, an outer edge of the top face outer region 14 on the top face 12 and an outer edge of the bottom face outer region 20 on the bottom face 17 of the elastic valve body 3 are connected by a substantially circumferential side face 50 constituting an outer wall of the elastic valve body together with the top face 12 and the bottom face 17.

[Top Face Cap 9]

Hereinafter, configurations of the top face cap 9, the bottom face cap 10, and the holder 8 will be described with reference to FIGS. 1 to 3.

As illustrated in FIGS. 2 and 3, the top face cap 9 includes a substantially cylindrical hollow barrel 22 and a flange 23 which is formed on one end of the hollow barrel 22. As illustrated in FIGS. 2 and 3, an edge 24 is located on an upper face (upper faces in FIGS. 2 and 3) positioned on the other end of the hollow barrel 22. The edge 24 defines a substantially circular insertion opening that is one end of the insertion section 5. A screw thread 25 is formed on the outer peripheral face of the hollow barrel 22 so as to be screwed with a lock connector defined by ISO 594. The flange 23 is a portion integrally molded with the hollow barrel 22. The flange 23 is engaged with the holder 8 (described later) and thereby the top face cap 9 is held by the holder 8.

As illustrated in FIGS. 2 and 3, the locking projection 26 is formed on an inner wall of the hollow barrel 22 near the edge 24. The locking projection 26 projects in the insertion direction B of the male connector 100 and enters the top face annular groove 15 of the elastic valve body 3 to compress the elastic valve body 3. An inner wall 27 formed between the edge 24 and the locking projection 26 is in contact with the top face central region 13 of the elastic valve body 3 when the male connector 100 is not inserted and is in contact with the male connector 100 when the male connector 100 is inserted (see FIG. 9, etc.). That is, when the male connector 100 is not inserted, the top face central region 13 is fitted into a space surrounded by the inner wall 27. On the other hand, when the male connector 100 is inserted, the male connector 100 is fitted with the top face cap 9 through the cylindrical inner wall 27. Although the inner wall 27 in the present embodiment has a cylindrical shape parallel to the insertion direction B, the inner wall 27 may have a tapered shape inner diameter of which is gradually reduced in the insertion direction B according to an outer shape of the male connector 100. In the present embodiment, the male connector 100 is fitted with the top face cap 9 through the cylindrical inner wall 27 when the male connector 100 is inserted; however, configurations thereof are not limited thereto and the male connector 100 may not be in contact with the cylindrical inner wall 27 when the male connector 100 is inserted.

The upper face of the hollow barrel 22 includes the aforementioned edge 24 and a planar extending section 28 which surrounds the edge 24 and extends in a direction C perpendicular to the insertion direction B. When the top face central region 13 of the elastic valve body 3 is fitted into a space surrounded by the inner wall 27, that is, when the male connector 100 is not inserted, the top face central region 13 of the elastic valve body 3 projects outward with respect to the edge 24 and the extending section 28 in a removal direction D (direction opposite to the insertion direction B) of the male connector 100. Allowing the top face central region 13 of the elastic valve body 3 to project in the removal direction D in the above manner enables the entire top face central region 13 to be easily wiped off in a wiping operation for disinfection typically performed by a user immediately before insertion of the male connector 100. As a result, the valve body 3 can be maintained in a sanitary condition without germs, foreign substances, or the like left thereon. The top face central region 13 of the elastic valve body 3 and the extending section 28 of the top face cap 9 may be configured to form the same plane with the top face central region 13 of the elastic valve body 3 housed up to a position (height) of the edge 24 when the male connector 100 is not inserted.

[Bottom Face Cap 10]

Like the top face cap 9, as illustrated in FIGS. 2 and 3, the bottom face cap 10 includes a substantially cylindrical hollow barrel 29 and a flange 30 which is formed on one end of the hollow barrel 29. The other end of the hollow barrel 29 is formed with the locking projection 31 which projects in the removal direction D, compresses the elastic valve body 3 while entering the aforementioned bottom face annular groove 21 of the elastic valve body 3, and clamps the elastic valve body 3 together with the locking projection 26 of the top face cap 9. In this manner, the elastic valve body 3 is compressed and clamped by the clamping section 32 including the aforementioned locking projection 26 of the top face cap 9 and the locking projection 31 of the bottom face cap 10 and thereby positioned and fixed in the hollow section 4, specifically, in the insertion section 5.

The bottom face cap 10 is ultrasonic-bonded to the inner face of the hollow barrel 22 and/or the lower face (the lower face in FIGS. 2 and 3) of the flange 23 of the top face cap 9 and thereby held by the top face cap 9. Furthermore, the position of the bottom face cap 10 is fixed by supporting the flange 30 of the bottom face cap 10 by the holder 8 (described below).

[Holder 8]

As illustrated in FIGS. 2 and 3, the holder 8 supports the top face cap 9 and the bottom face cap 10 and defines the flow path 6 therein. In the present embodiment, the holder 8 are directly in contact with and thereby holds both of the top face cap 9 and the bottom face cap 10; however, for example, the holder 8 may not be in contact with the top face cap 9 but in direct contact with only the bottom face cap 10, thereby allowing the top face cap 9 to be in contact with the bottom face cap 10 and to be supported thereby. That is, the holder 8 may be in direct contact with and support one of the top face cap 9 and the bottom face cap 10 while not contacting the other. Preferably, members that are in direct contact are bonded by ultrasonic-bonding or the like, for example.

In the present embodiment, the top face cap 9 and the bottom face cap 10 clamps the elastic valve body 3 and thereby holds the elastic valve body 3 within the insertion section 5; however, for example, a holder integrally including the holder 8 and the bottom face cap 10 as in the present embodiment and the top face cap as in the present embodiment may compress and clamp the elastic valve body 3. That is, the housing of the connector is not limited to that including three members of a holder, a top face cap, and a bottom face cap but may be configured by two members out of the above members, for example. Furthermore, by adding another (other) member(s) to the above members, thereby configuring the housing by four or more members.

Next, detailed configuration of the holder 8 of the present embodiment will be described. As illustrated in FIGS. 2 and 3, the holder 8 of the present embodiment includes a substantially cylindrical outer barrel 34 which has a screw thread 33 for a lock connector formed on an inner peripheral face thereof, a male luer section 35, as an inner barrel, formed in a hollow section defined by an inner wall of the outer barrel 34, and a connection section 36 connecting the outer barrel 34 and the male luer section 35 at an end on the upstream side of the insertion direction B (downstream side of the removal direction D) of the outer barrel 34 and the male luer section 35. In the holder 8 of the present embodiment, an inner wall of the male luer section 35 and an inner wall of the connection section 36 define the flow path 6.

The flow path 6 defined by the holder 8 of the present embodiment includes a tubular flow path 37 defined by the inner wall of the male luer section 35 having a tapered shape where an inner diameter becomes smaller toward the downstream side of the insertion direction B and a connection flow path 38, defined by the connection section 36, positioned between the insertion section 5 and the tubular flow path 37 in the insertion direction B and connecting the insertion section 5 and the tubular flow path 37.

As illustrated in FIGS. 2 and 3, the inner wall of the housing 2 defining the flow path 6 is integrally formed with a liquid barrier face 39 which faces a tip opening 104 of the male connector 100 (see FIG. 9, etc.) inserted in the insertion section 5 in the insertion direction B and collides with liquid flowing out from the tip opening 104. In the present embodiment, an inner wall of the connection section 36 defining the connection flow path 38 of the flow path 6 is integrally formed with the liquid barrier face 39. That is, the liquid barrier face 39 itself is a part of the inner wall defining the flow path 6. Moreover, the liquid barrier face 39 is formed in the member itself having the inner wall defining the flow path 6.

In other words, the liquid barrier face 39 of the present embodiment is included in a partition section 40 of the housing 2. Specifically, the housing 2 of the present embodiment includes the partition section 40 dividing the flow path 6 in the direction C perpendicular to the insertion direction B and the liquid barrier face 39 includes an upstream face 41 (upper face in FIGS. 2 and 3) which is a face of the partition section 40 on the upstream side of the insertion direction B. More specifically, the holder 8 of the housing 2 of the present embodiment includes the partition section 40 dividing the connection flow path 38 into a plurality of separated flow paths (in the present embodiment, two separated flow paths) in the direction C perpendicular to the insertion direction B. The liquid barrier face 39 is formed by the upstream face 41 of the partition section 40.

The holder 8 of the housing 2 of the present embodiment includes the partition section 40 having the upstream face 41 as the liquid barrier face 39 as described above and thus liquid such as a liquid medicine supplied from the tip opening 104 (see FIG. 9, etc.) of the male connector 100 inserted in the insertion section 5 of the connector 1 into the flow path 6 of the connector 1 collides on the upstream face 41 as the liquid barrier face 39, thereby generating a turbulence flow in the flow path 6. This allows for suppressing continuous stagnation of liquid such as liquid medicine in the hollow section 4 of the connector 1. The configuration of the partition section 40 will be described in detail later (see FIGS. 6 to 8, etc.).

As illustrated in FIGS. 2 and 3, the inner wall, defining the flow path 6, of the housing 2 of the present embodiment includes a tip receiving face 42 to receive the tip 101 (see FIGS. 9 to 11) of the male connector 100. The tip receiving face 42 receives the tip 101 of the male connector 100 inserted from the outside through the slit 11 of the elastic valve body 3 and thereby prevents the male connector 100 from being excessively inserted into the connector 1 in the insertion direction B of the male connector.

More specifically, the tip receiving face 42 of the present embodiment is integrally formed with the inner wall of the holder 8 defining the connection flow path 38. The tip receiving face 42 of the present embodiment is positioned on the upstream side with respect to the upstream face 41 in the insertion direction B. Therefore, when the tip 101 of the male connector 100 inserted in the insertion section 5 is received by the tip receiving face 42, a space is formed between the tip opening 104 of the male connector 100 and the upstream face 41 of the partition section 40. As illustrated in FIG. 3, the tip receiving face 42 of the present embodiment is integrally formed with the aforementioned upstream face 41 of the partition section 40 in a continuous manner. Details of the tip receiving face 42 will be described later (see FIGS. 9 to 11, etc.).

[Partition Section 40]

Figure 6:
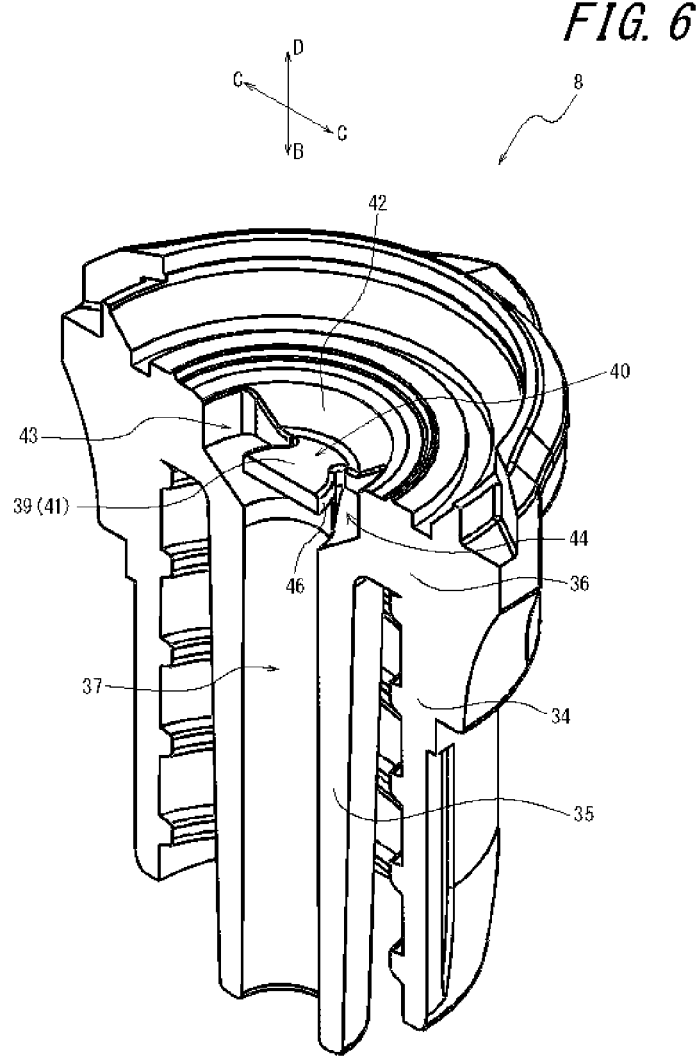
FIG. 6 is a cross-sectional perspective view of a holder alone illustrating the same cross section as that of the connector illustrated in FIG. 2.
Figure 7:
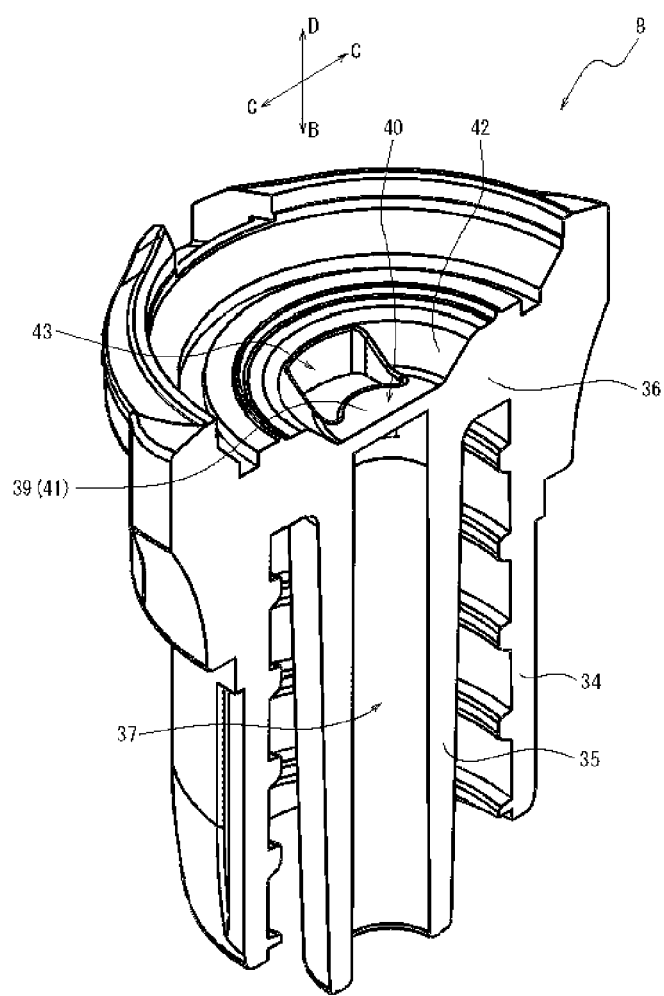
FIG. 7 is a cross-sectional perspective view of the holder alone illustrating the same cross section as that of the connector illustrated in FIG. 3.
Figure 8:
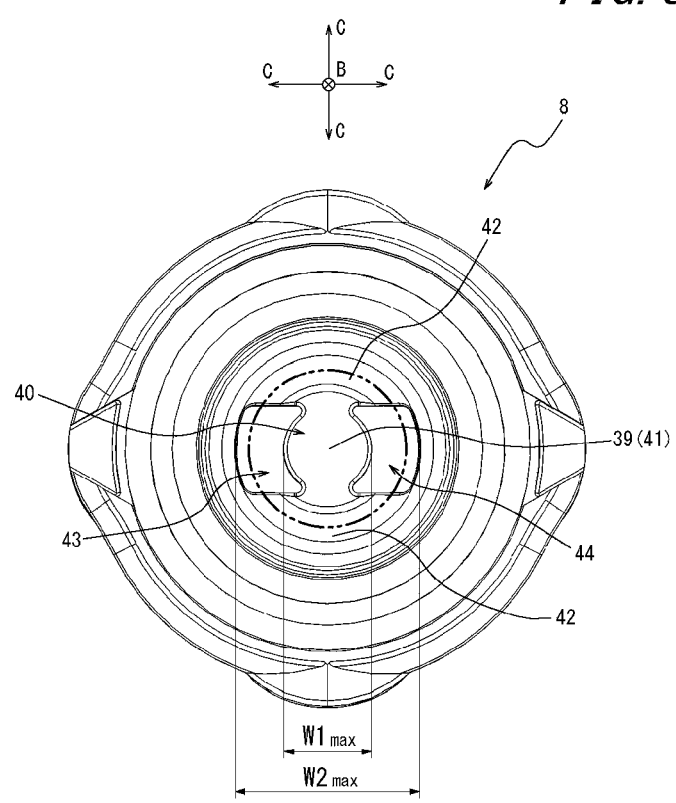
FIG. 8 is a top view of the holder alone seen from an insertion direction of a male connector.

Next, detailed configuration of the partition section 40 will be described. FIG. 6 is a cross-sectional perspective view of the holder 8 alone illustrating the same cross section as that of the connector 1 illustrated in FIG. 2. Moreover, FIG. 7 is a cross-sectional perspective view of the holder 8 alone illustrating the same cross section as that of the connector 1 illustrated in FIG. 3. Furthermore, FIG. 8 is a top view of the holder 8 seen from the insertion direction B. For convenience of description, a round two-dot chain line illustrated in FIG. 8 represents the position of the edge 24 of the top face cap 9 attached to the holder 8. Hereinafter, the partition section 40 will be described in detail with reference to FIGS. 2, 3, and 6 to 8.

As described above, the upstream face 41 of the partition section 40 forms the aforementioned liquid barrier face 39 and the partition section 40 divides the flow path 6 in the direction C perpendicular to the insertion direction B. As illustrated in FIGS. 6 to 8, the partition section 40 of the present embodiment extends to connect opposite inner walls in the direction C perpendicular to the insertion direction B and divides the flow path 6 into two separated flow paths in a direction perpendicular to the opposing direction of the opposite inner walls out of the directions C perpendicular to the insertion direction B. More specifically, the partition section 40 of the present embodiment divides the connection flow path 38 of the flow path 6 into a first connection flow path 43 and a second connection flow path 44 separated from each other. Liquid flowing out from the tip opening 104 (see FIG. 9, etc.) of the male connector 100 inserted in the insertion section 5 is bifurcated by the partition section 40, passes through the first connection flow path 43 and the second connection flow path 44, and then joins in the tubular flow path 37.

The partition section 40 of the present embodiment has a plate shape and includes the upstream face 41 as the liquid barrier face 39, a downstream face 45 which is the opposite face of the upstream face 41 (face on the downstream side in the insertion direction B), and a side face 46 connecting the upstream face 41 and the downstream face 45.

In the present embodiment, both of the upstream face 41 and the downstream face 45 are planes extending in the direction C perpendicular to the insertion direction B. In the present embodiment, therefore, when the male connector 100 is inserted in the insertion section 5, the liquid flowing out from the tip opening 104 of the male connector 100 collides on the upstream face 41 (liquid barrier face 39) and then flows in the direction C perpendicular to the insertion direction B along the planar upstream face 41. As a result, the liquid flowing out from the tip opening 104 easily reaches an inner wall defining the connection flow path 38 positioned around the partition section 40 in the direction C perpendicular to the insertion direction B. This allows for forming a flow of liquid in such a manner as to follow along the inner wall defining the flow path 6, thereby further mitigating continuous stagnation of liquid in the hollow section 4.

Furthermore, the upstream face 41 as the liquid barrier face 39 is included at a position overlapping with the insertion opening, defined by the inner wall of the housing 2, which is the end of the insertion section 5 when seen from the insertion direction B of the housing 2. Specifically, as illustrated in FIG. 8, the upstream face 41 is included at a position overlapping with the insertion opening (opening, defined by the edge 24, illustrated by the two-dot chain line in FIG. 8) that is the end of the insertion section 5. Especially in the present embodiment, the entire region of the upstream face 41 is positioned on the inner side with respect to the insertion opening that is the end of the insertion section 5 when the housing 2 is seen from the insertion direction B. Furthermore, the upstream face 41 is positioned to overlap at least with the central region of the insertion opening (see FIG. 8). Positioning the upstream face 41 at such a position allows the upstream face 41 to face the tip opening 104 (see FIGS. 9 to 11) of the male connector 100 inserted from the outside in the insertion direction B. In other words, the upstream face 41 of the present embodiment is positioned on the upstream side with respect to the tubular flow path 37 in the insertion direction B.

The phrase "when the housing 2 is seen from the insertion direction B" refers to a case where an object is projected on a virtual plane when the housing 2 is seen from the insertion direction B and does not mean whether visual inspection is actually possible. Therefore, the above relation between the upstream face 41 and the insertion opening refers to a case where the upstream face 41 and the inner wall of the housing 2 (in the present embodiment, the edge 24) defining the insertion opening are projected on a virtual plane when the housing 2 is seen from the insertion direction B.

Furthermore in the present embodiment, when the housing 2 including the holder 8, the top face cap 9, and the bottom face cap 10 is seen from the insertion direction B, the maximum width W1max of a width W1 of the partition section 40 interposed between the flow paths 6 is smaller than an internal diameter d of the housing 2 defining the insertion opening that is the end of the insertion section 5. More specifically, as illustrated in FIG. 2, the maximum width W1max of the partition section 40 interposed between the first connection flow path 43 and the second connection flow path 44 is smaller than the internal diameter d of the edge 24 of the top face cap 9.

Moreover, as illustrated in FIG. 2, the maximum width W2max of a width W2 of the inner wall defining the connection flow path 38 in the direction C perpendicular to the insertion direction B is larger than the internal diameter d of the housing 2 defining the insertion opening that is the end of the insertion section 5. That is, in the present embodiment, an inequality W1max<d<W2max holds. According to the connector 1 of the present embodiment, therefore, the partition section 40 included in the housing 2 generates a turbulence flow of liquid, thereby allowing for mitigating continuous stagnation of the liquid in the hollow section 4. Also, since relatively large spaces are ensured for the flow paths (in the present embodiment, the first connection flow path 43 and the second connection flow path 44) positioned in the direction C perpendicular to the insertion direction B with respect to the partition section 40, a flow rate per unit time of the liquid flowing in the flow path 6 tends not to be limited by the partition section 40. The above maximum width W2max is positioned in the direction C perpendicular to the insertion direction B with respect to the partition section 40 and refers to the maximum distance between the inner walls opposite to each other interposing the flow paths 6 (in the present embodiment, the first connection flow path 43 and the second connection flow path 44) and the partition section 40 in the direction C.

As illustrated in FIG. 8, the partition section 40 of the present embodiment has a substantially round-shaped outer shape when seen from the insertion direction B. That is, the upstream face 41 and the downstream face 45 of the present embodiment are planes having a substantially round-shaped outer shape of the same outer diameter. A side face 46 connects outer edges of the upstream face 41 and the downstream face 45 and is an arc-shaped curved face when seen from the insertion direction B. Therefore, the above the maximum width W1max of the present embodiment is equivalent to an outer diameter of the partition section 40, that is, an outer diameter of the upstream face 41 or the downstream face 45 when seen from the insertion direction B.

The partition section 40 of the present embodiment extends to connect the opposite inner walls in the direction C perpendicular to the insertion direction B and forms the two separated flow paths in a direction perpendicular to the opposing direction of the opposite inner walls out of the directions C perpendicular to the insertion direction B. However, for example, a partition section may protrude from one side toward the other side of the opposite inner walls in the direction C perpendicular to the insertion direction B and may not be connected to the other side where apart of the partition section is connected in the direction C perpendicular to the insertion direction B, thereby forming one flow path. Moreover, the partition section 40 of the present embodiment extends to connect opposite inner walls in the direction C perpendicular to the insertion direction B; however, the positions where the partition section 40 extends from and to are not limited thereto and, for example, a partition section may extend to connect inner walls that are not opposite to each other in the direction C perpendicular to the insertion direction B. Furthermore, the number of flow paths separated by the partition section is not limited to two and a partition section may divide a flow path into three or more flow paths separated from each other.

The upstream face 41 of the present embodiment is a plane extending in the direction C perpendicular to the insertion direction B. However, the upstream face is not limited to such a plane as long as a shape thereof facilitates formation of a flow of liquid in such a manner as to follow along an inner wall defining the flow path 6. Therefore, for example, an upstream face 41 may be a plane inclined by a predetermined angle with respect to the direction C perpendicular to the insertion direction B or may be a curved face bent toward the insertion direction B or the removal direction D. Note that it is especially preferable that, like in the present embodiment, the upstream face 41 of the partition section 40 is a plane extending in the direction C perpendicular to the insertion direction B. This allows for facilitating formation of a flow of liquid in such a manner as to follow along an inner wall defining the flow path 6 as well as suppressing stagnation of liquid such as liquid medicine on the upstream face 41 after use of the connector 1, for example.

The downstream face 45 of the partition section 40 of the present embodiment is a plane extending in the direction C perpendicular to the insertion direction B and the side face 46 is a curved face without an inflection point; however, the downstream face or the side face is not limited thereto. Note that configuring the respective faces included in the outer wall by planes or curved faces without inflection points like the partition section 40 of the present embodiment results in not forming a part prone to stagnation of liquid on the respective faces such as a corner between a groove wall and a groove bottom, thereby further suppressing stagnation of liquid on the respective faces.

Moreover, as illustrated in FIG. 8, the partition section 40 of the present embodiment is a round flat plate having a substantially round-shaped outer shape when seen from the insertion direction B; however, the partition section 40 is not limited thereto. For example, the partition section 40 may have a columnar shape such as a rectangular parallelepiped or a cube having two linear lines, parallel to each other when seen from the insertion direction B, as a contour of an outer edge. Alternatively, the partition section may be a combination of a plurality of three-dimensional shapes. For example, a partition section may be formed of a columnar round flat plate section having a liquid barrier face and a plurality of rod-shaped sections which extends from a side face of the round flat plate section toward a radial direction and connects an inner wall of a flow path positioned around the round flat plate section with the round flat plate section. The above the maximum width W1max of the partition section having such a configuration is equivalent to an outer diameter of the round flat plate section.

Figure 13:
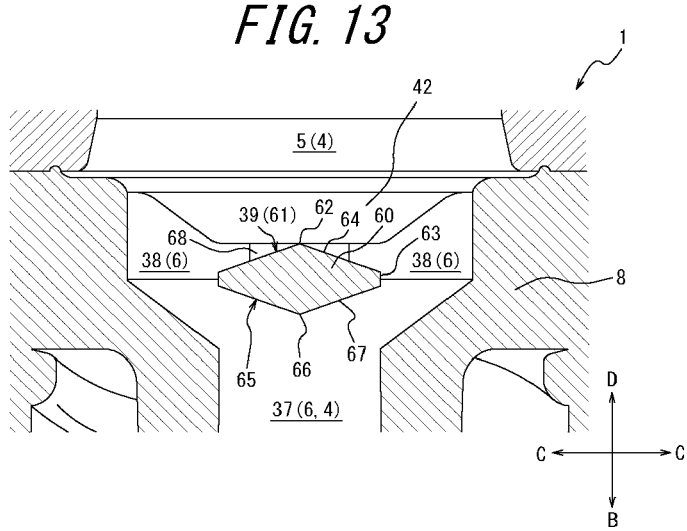
FIG. 13 is a cross-sectional view illustrating a modification of a partition section in the connector illustrated in FIG. 1.

FIG. 13 is a diagram illustrating a partition section 60 as a modification of the partition section 40 of the present embodiment. FIG. 13 is an enlarged cross-sectional view of the partition section 60 in the same cross section as that in FIG. 2. An upstream face 61 as a liquid barrier face 39 of the partition section 60 illustrated in FIG. 13 expands from an apex 62 on the removal direction D side toward the insertion direction B and has a side face shape of a cone formed by an inclined face 64 where an end on the insertion direction B side communicates with a side face 63. Such a shape of the upstream face 61 facilitates liquid such as liquid medicine colliding on the upstream face 61 to be guided into a connection flow path 38 along the inclined face 64 as compared to the upstream face 41 of the partition section 40 of the present embodiment. That is, on the upstream face 61, including the inclined face 64 inclined toward the connection flow path 38 descending from the upstream side to the downstream side of the insertion direction B facilitates ensuring a flow rate per unit time of liquid flowing from an insertion section 5 side toward a tubular flow path 37, thereby allowing for shortening time required for removal of liquid stagnating in a hollow section 4. The upstream face 61 illustrated in FIG. 13 has no convex curved portion toward the insertion direction B, thereby suppressing stagnation of liquid such as liquid medicine on the upstream face 61 after use of a connector 1, for example.

Moreover, a downstream face 65 of the partition section 60 illustrated in FIG. 13 expands from an apex 66 on the insertion direction B toward the removal direction D and has a side face shape of a cone formed by an inclined face 67 where an end on the removal direction D side communicates with the side face 63. Such a shape of the downstream face 65 allows for mitigating stagnation of liquid on the downstream face 65 as compared to the downstream face 45 of the partition section 40 of the present embodiment.

The upstream face 61 of the partition section 60 illustrated in FIG. 13 is integrally formed with an inner wall defining the connection flow path 38 as the flow path 6 like the upstream face 41 of the partition section 40 of the present embodiment. Specifically, the upstream face 61 is integrally formed with a tip receiving face 42 defining the connection flow path 38. More specifically, the upstream face 61 is integrally formed with the tip receiving face 42 via a step face 68 integrally formed with the tip receiving face 42 in a continuous manner.

The partition section 60 illustrated in FIG. 13 has different shapes of the upstream face 61 and a downstream face 65 as compared to those of the partition section 40 of the present embodiment. However, other configurations are similar.

Figure 14:
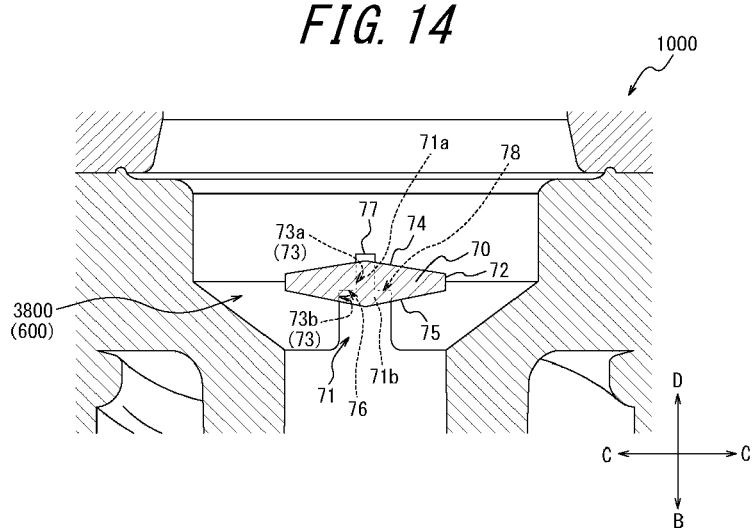
FIG. 14 is an enlarged cross-sectional view of a connector including a partition member having a similar shape to that of the partition section illustrated in FIG. 13.

FIG. 14 is a diagram illustrating of a partition member 70 having a similar shape to that of the partition section 60 illustrated in FIG. 13. More specifically, FIG. 14 is an enlarged cross-sectional view illustrating the enlarged partition member 70 at a similar cross section to that in FIG. 2 of a connector 1000 attached with the partition member 70. The partition member 70 illustrated in FIG. 14 is attached to a support section 71 of a rib shape integrally formed with an inner wall defining a connection flow path 3800 as a flow path 600 and thereby supported by the support section 71. The partition member 70 illustrated in FIG. 14 is formed with a cut-away section 73, where the support section 71 enters, at a position opposite to the side face 72 (in the example illustrated in FIG. 14, position opposite in a direction perpendicular to the paper face). The cut-away section 73 extends from an upstream face 74 to a downstream face 75 and includes an upstream side cut-away section 73a on the upstream face 74 side and a downstream side cut-away section 73b which communicates with the upstream side cut-away section 73a via a step face 76 and has a larger width than that of the upstream side cut-away section 73a in the direction C perpendicular to the insertion direction B. The support section 71 has a shape corresponding to the cut-away section 73 and an end thereof on the removal direction D side includes a tip receiving face 77 to receive a tip 101 (see FIG. 9, etc.) of the male connector 100. The support section 71 includes a first fitting section 71a which fits into the upstream side cut-away section 73a and a second fitting section 71b which fits into the downstream side cut-away section 73b and has a larger width than that of the first fitting section 71a in the direction C perpendicular to the insertion direction B. A step face 78 between an outer face of the first fitting section 71a and an outer face of the second fitting section 71b abuts against the step face 76 of the cut-away section 73 and thereby limits further movement of the attached partition member 70 in the insertion direction B. That is, the partition member 70 is positioned with respect to the support section 71 in the insertion direction B with the step face 76 of the partition member 70 abutting against the step face 78 of the support section 71.

Figure 15:
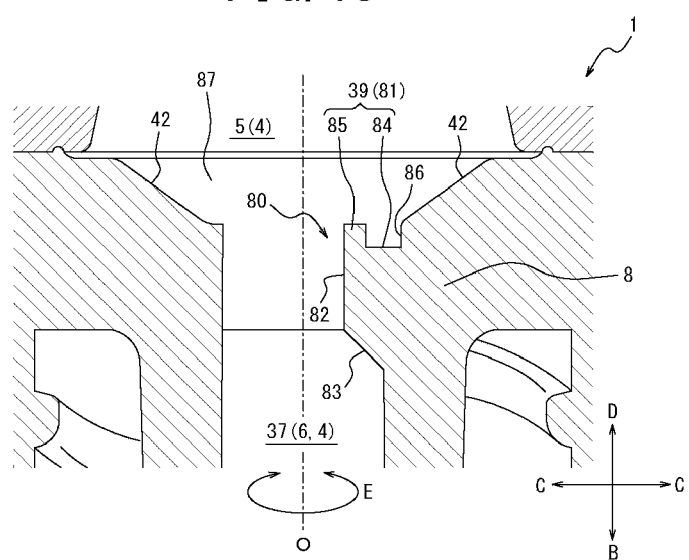
FIG. 15 is a cross-sectional view illustrating a modification of a liquid barrier face in the connector illustrated in FIG. 1.
Figure 16:
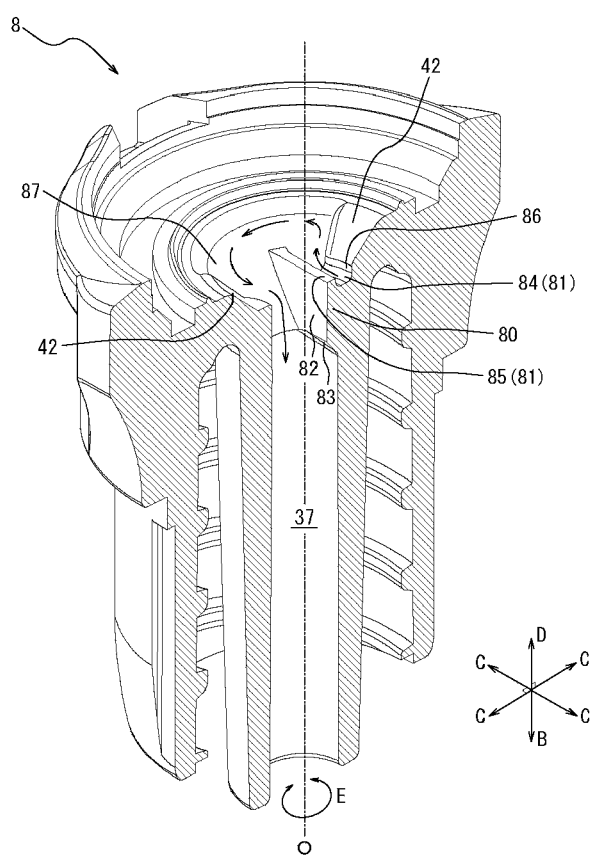
FIG. 16 is a cross-sectional perspective view, of the holder alone including a projecting wall section illustrated in FIG. 15, illustrating the same cross section as that of the connector illustrated in FIG. 3.

FIG. 15 is a diagram illustrating a modification of the liquid barrier face 39 of the present embodiment. Specifically, FIG. 15 is a diagram illustrating a connector 1 including a projecting wall section 80 instead of the partition section 40 as well as an enlarged cross-sectional view of the projecting wall section 80 at the same cross section as that in FIG. 3. FIG. 16 is a cross-sectional perspective view, of a holder 8 alone including the projecting wall section 80, illustrating the same cross section as that of the connector 1 illustrated in FIG. 3. The projecting wall section 80 illustrated in FIGS. 15 and 16 is integrally formed with an inner wall defining a flow path 6 and projects inward (in FIG. 15, toward the central axis O of a tubular flow path 37) from the surrounding inner wall positioned in the direction C perpendicular to the insertion direction B In other words, a housing 2 (see FIG. 2, etc.) includes the projecting wall section 80 projecting inward from the surrounding inner wall positioned in the direction C perpendicular to the insertion direction B.

As illustrated in FIG. 15, the projecting wall section 80 includes an upstream face 81 as a liquid barrier face 39, a side face 82 communicating with an edge of the upstream face 81 on the flow path 6 side and extending in the insertion direction B, and a downstream face 83 communicating with an end of the side face 82 in the insertion direction B and formed by an inclined face expanding outward in the radial direction of the flow path 6 in the insertion direction B.

The upstream face 81 as the liquid barrier face 39 of the projecting wall section 80 is a face of the projecting wall section 80 on the upstream side in the insertion direction B, that is, a face on the removal direction D side of the projecting wall section 80. The upstream face 81 includes a planar section 84 extending in the direction C perpendicular to the insertion direction B and a rib-shaped projection 85 integrally formed with the planar section 84 and projecting from the planar section 84 in the removal direction D.

The planar section 84 illustrated in FIGS. 15 and 16 is integrally formed with a tip receiving face 42 to receive a tip 101 (see FIG. 9, etc.) of a male connector 100 via a step face 86.

As illustrated in FIG. 16, the tip receiving face 42 is formed at a part of an inner wall defining a flow path 6 in a circumferential direction E around the central axis O. The tip receiving face 42 projects inward of the flow path 6 than other parts in the circumferential direction E. In other words, of the inner wall defining the flow path 6, a part adjacent to the tip receiving face 42 in the circumferential direction E is a diameter expansion face 87 positioned outward in the radial direction of the flow path 6 than the tip receiving face 42 via the step. As illustrated in FIGS. 15 and 16, the tip receiving faces 42 are included at opposite positions interposing the flow path 6. The diameter expansion faces 87 are arranged opposite to each other interposing the flow path 6, of the directions C perpendicular to the insertion direction B, in a direction perpendicular to the opposing direction of the two tip receiving faces 42. In other words, the diameter expansion faces 87 are positioned between the two opposite tip receiving faces 42 in the circumferential direction E. The diameter expansion face 87 may be formed as a reduced thickness portion, for example. As illustrated in FIG. 16, the opposite diameter expansion faces 87 have a bent tapered shape where an opposing distance in the direction C perpendicular to the insertion direction B gradually decreases in the insertion direction B. An end of the diameter expansion face 87 in the insertion direction B is communicated with an inner wall defining a tubular flow path 37.

The rib-shaped projection 85 illustrated in FIGS. 15 and 16 extends, of the directions C perpendicular to the insertion direction B, in the direction perpendicular to the opposing direction of the tip receiving faces 42. In other words, the rib-shaped projection 85 extends in the opposing direction of the opposing diameter expansion faces 87. Both ends of the rib-shaped projection 85 in the extending direction are integrally formed with the diameter expansion faces 87 in a continuous manner.

Therefore, as illustrated in FIGS. 15 and 16, the planar section 84 of the upstream face 81 forms a bottom section of a concave section defined by a face of the rib-shaped projection 85 on the outer side in the radial direction of the flow path 6, the tip receiving face 42, the step face 86 communicating with the tip receiving face 42, and the diameter expansion faces 87 opposite to each other.

When the male connector 100 is inserted in the connector 1, the tip receiving face 42 directly or indirectly receives the tip 101 of the male connector 100, thereby positioning the male connector 100 in the insertion direction B. In a state where the male connector 100 is positioned by the tip receiving face 42, a space is formed between the male connector 100 and the diameter expansion face 87.

The side face 82 of the projecting wall section 80 extends in the insertion direction B to smoothly communicate with a face of the rib-shaped projection 85 on the inner side in the radial direction of the flow path 6.

Including such a projecting wall section 80 allows liquid flowing in from the tip 101 of the male connector 100 connected to the connector 1 collides on the upstream face 81 as the liquid barrier face 39 and then generates a turbulence flow. Specifically, as illustrated by arrows in FIG. 16, a flow is formed where the liquid flows from the planar section 84 interposed between the rib-shaped projection 85 and the step face 86, passes through the space formed between the male connector 100 and the diameter expansion face 87, then flows along the diameter expansion face 87 in the circumferential direction E, climbs over the rib-shaped projection 85 of the projecting wall section 80, and flows in the insertion direction B toward the tubular flow path 37. That is, since a flow along the inner wall defining the hollow section 4 of the connector 1 is formed, continuous stagnation of liquid in the hollow section 4 can be mitigated.

Furthermore, the connector 1 illustrated in FIGS. 15 and 16 includes, at a position adjacent to the tip receiving face 42 in the circumferential direction E, the diameter expansion face 87 on the outer side than the tip receiving face 42 in the radial direction. This allows liquid to flow through the position on the outer side in the radial direction where liquid is prone to stagnation, thereby further suppressing stagnation of liquid in the hollow section 4.

The downstream face 83 of the projecting wall section 80 illustrated in FIGS. 15 and 16 is an inclined face inclined toward the insertion direction B. Therefore, as compared to a case of a plane perpendicular to the insertion direction B, liquid tends not to stagnate on the downstream face 83.

The upstream face 81 of the projecting wall section 80 illustrated in FIGS. 15 and 16 collides only with a part of the liquid flowing in from the tip 101 of the male connector 100 inserted in the connector 1. That is, when the projecting wall section 80 is seen from the insertion direction B, an area of the projecting wall section 80 is smaller than an area of the partition section 60 illustrated in FIG. 13. Thus, a part of the liquid flowing in from the tip 101 of the male connector 100 inserted in the connector 1 flows toward the tubular flow path 37 without colliding on the upstream face 81. Therefore, with the projecting wall section 80 illustrated in FIGS. 15 and 16, it is further easier to secure a flow rate per unit time of liquid flowing from the insertion section 5 side toward the tubular flow path 37 as compared to the partition section 60 illustrated in FIG. 13. Especially, the projecting wall section 80 illustrated in FIGS. 15 and 16 is not arranged on the central axis O of the tubular flow path 37 when the connector 1 is seen from the insertion direction B. Therefore, the projecting wall section 80 is arranged in a projecting manner such that the projecting wall section 80 and the tip opening 104, (see FIG. 9, etc.) of the male connector 100 inserted such that the central axis thereof and the central axis O of the tubular flow path 37 substantially matches, overlap with each other at a different position from the central axis O when seen from the insertion direction B. Therefore, the projecting wall section 80 has a configuration that further facilitates securing a flow rate per unit time of liquid flowing from the insertion section 5 side toward the tubular flow path 37. Furthermore, the projecting wall section 80 illustrated in FIGS. 15 and 16 can be molded by one mold and thus is advantageous in the point that a mold structure can be simplified.

Figure 17:
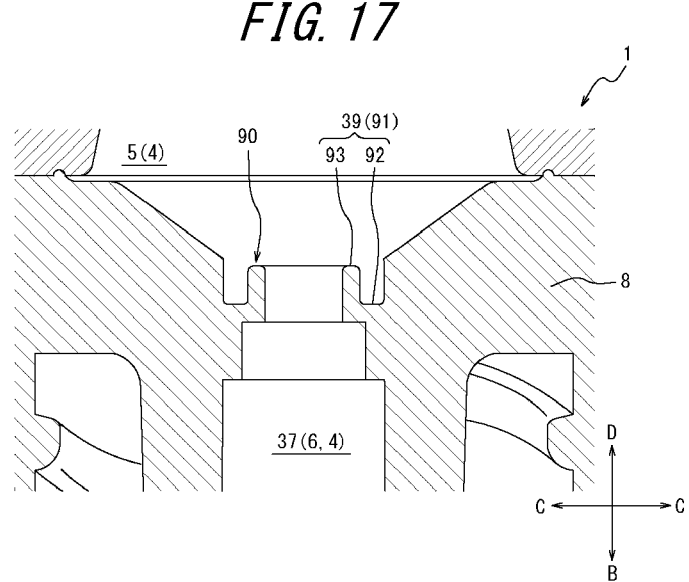
FIG. 17 is a cross-sectional view illustrating a modification of a liquid barrier face in the connector illustrated in FIG. 1.

FIG. 17 is a diagram illustrating another modification of the liquid barrier face 39 of the present embodiment. Specifically, FIG. 17 is a diagram illustrating a connector 1 including an annular flange 90 instead of the partition section 40 as well as an enlarged cross-sectional view of the annular flange 90 at the same cross section as that in FIG. 3. The annular flange 90 projects from an inner peripheral face of a flow path 6 toward the inner side of the flow path 6 in the direction C perpendicular to the insertion direction B and is integrally formed with an inner wall defining the flow path 6. In other words, a housing 2 (see FIG. 2, etc.) includes the annular flange 90 projecting toward the inner side of the flow path 6. An upstream face 91 as a liquid barrier face 39 of the annular flange 90 is a face of the annular flange 90 on the upstream side in the insertion direction B. The upstream face 91 includes a planar section 92 extending in the direction C perpendicular to the insertion direction B and an annular rib 93 projecting from an inner edge of the planar section 92 in the removal direction D. Since the upstream face 91 includes the annular rib 93, liquid flowing in from a tip 101 of an inserted male connector 100 and colliding on the planar section 92 is limited of a flowing direction by the annular rib 93 and thus tends to flow in the circumferential direction E along an inner wall defining the flow path 6. That is, since a flow along the inner wall defining the flow path 6 is formed, continuous stagnation of liquid in the hollow section 4 can be mitigated.

A tip receiving face 42 illustrated in FIG. 17 has the same configuration as those illustrated in FIGS. 15 and 16. Moreover, preferably, an inner wall of a part adjacent to the tip receiving face 42, illustrated in FIG. 17, in the circumferential direction E is positioned outward in the radial direction of the flow path 6 than the tip receiving face 42 like the diameter expansion face 87 illustrated in FIGS. 15 and 16.

[Connector 1 where Male Connector 100 is Inserted from Outside]

Figure 9:
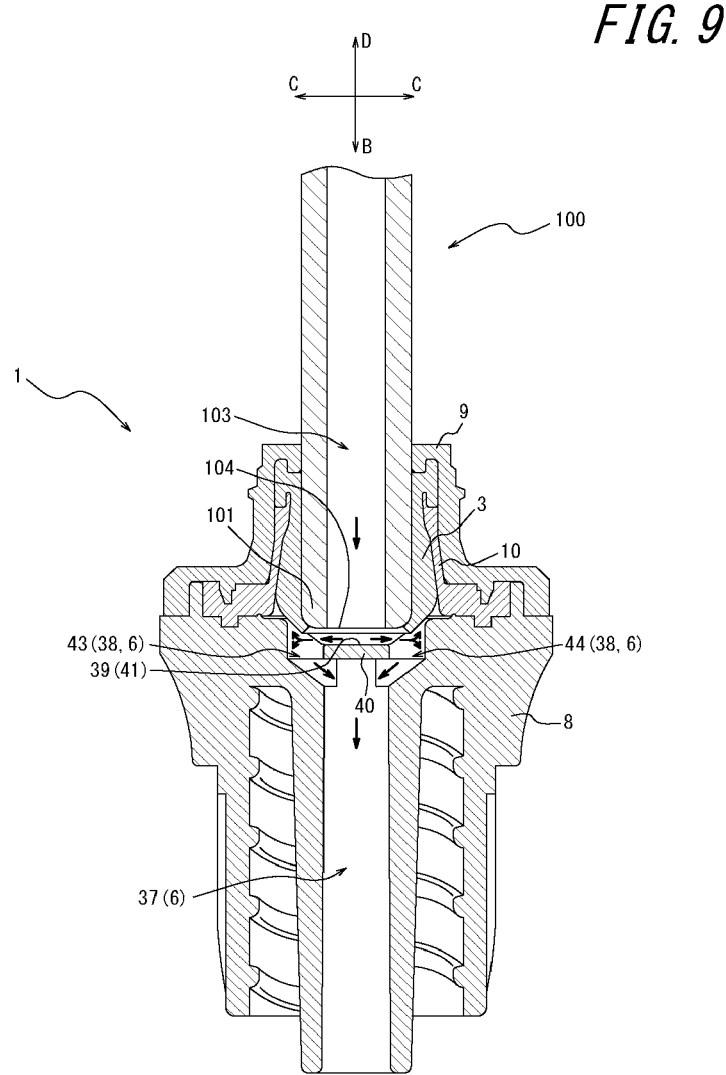
FIG. 9 is a cross-sectional view, of the connector inserted with the male connector, illustrating the same cross section as that in FIG. 2.
Figure 10:
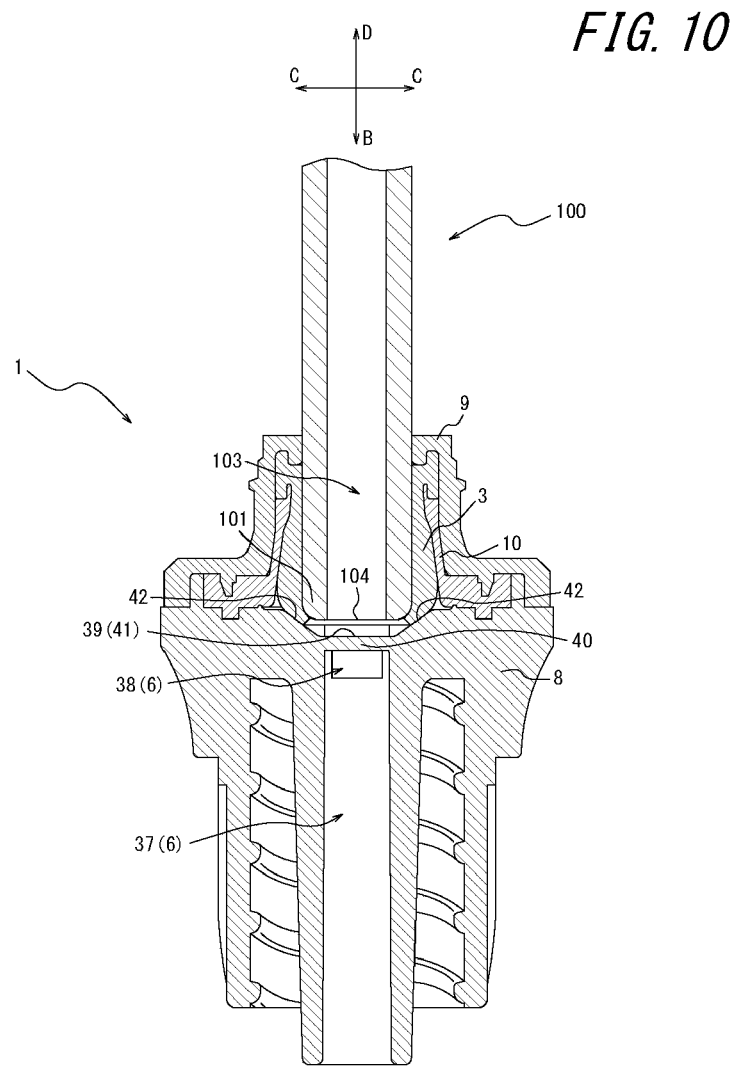
FIG. 10 is a cross-sectional view, of the connector inserted with the male connector, illustrating the same cross section as that in FIG. 3.
Figure 11:
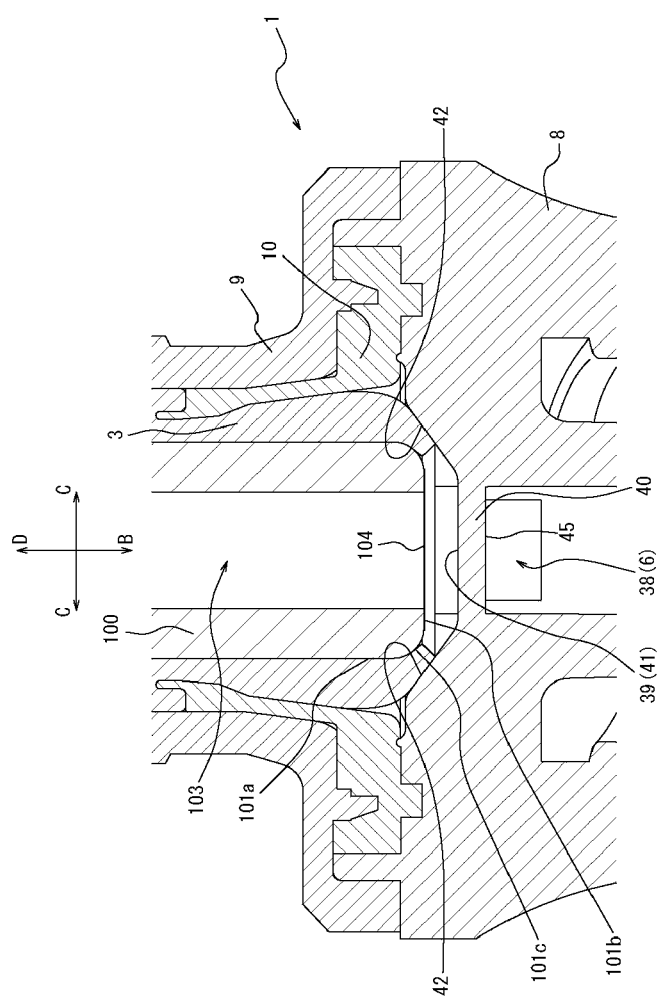
FIG. 11 is an enlarged cross-sectional view where a tip and the vicinity thereof of the male connector are enlarged from the cross section illustrated in FIG. 10.

In the above, descriptions have been provided mainly on the configurations of the connector 1 where the male connector 100 is not inserted from the outside as illustrated in FIGS. 1 to 8. Hereinafter, the connector 1 where the male connector 100 is inserted in the insertion section 5 from the outside will be described. FIG. 9 is a cross-sectional view, of a connector 1 inserted with a male connector 100, illustrating the same cross section as that illustrated in FIG. 2. FIG. 10 is a cross-sectional view, of the connector 1 inserted with the male connector 100, illustrating the same cross section as that illustrated in FIG. 3. FIG. 11 is an enlarged cross-sectional view where a tip 101 and the vicinity thereof of the male connector 100 are enlarged from FIG. 10.

First, the male connector 100 inserted into the connector 1 will be described. The male connector 100 has a shape defined by ISO 594 with an outer diameter of a cross section perpendicular to the insertion direction B of the male connector gradually decreasing by 6% for every 1 mm toward a tip 101 in a tapered manner. More specifically, the male connector 100 can be formed of the same material as that of the aforementioned housing 2. When the male connector 100 is formed of a rigid material, a diameter of the tip is within a range of 3.925 mm to 3.990 mm. When the male connector 100 is formed of a semi-rigid material, a diameter of the tip is within a range of 3.925 mm to 4.027 mm. The length of the male connector 100 is 7.50 mm or more.

When the male connector 100 is inserted into the insertion section 5 (see FIG. 2, etc.) of the connector 1, the tip 101 of the male connector 100 elastically deforms the elastic valve body 3 in a pushing manner toward the inner side of the connector 1 and reaches the flow path 6 in the holder 8 via the slit 11. That is, in the present embodiment, in a state illustrated in FIGS. 9 to 11, a flow path 103 in the male connector 100 is directly communicating with the flow path 6 of the holder 8.

The elastic valve body 3 is elastically deformed by the inserted male connector 100, enters between the inner wall of the bottom face cap 10 and an outer wall of the male connector 100, and is tightly attached to an outer face of the male connector 100. This suppresses leakage of liquid from the insertion section 5 of the connector 1 to the outside.

As illustrated in FIG. 10, the tip 101 of the male connector 100 abuts against the tip receiving face 42 provided to the inner wall defining the connection flow path 38 of the inner wall of the holder 8 while interposing the elastic valve body 3, thereby positioning the male connector in the insertion direction B. More specifically, as illustrated in FIG. 11, the tip 101 of the male connector 100 includes a tip peripheral face 101a forming the outer wall of the male connector in the direction C perpendicular to the insertion direction B, a tip plane 101b defining a tip opening 104 of the flow path 103 in the male connector 100 and forming the outer wall of the male connector in the insertion direction B, and a tip curved face 101c having an arc-shaped cross section and connecting the tip peripheral face 101a and the tip plane 101b in the cross-sectional view in FIGS. 9 to 11. The tip curved face 101c of the tip 101 of the male connector 100 presses the tip receiving face 42 via the elastic valve body 3, thereby limiting insertion of the male connector 100 in the insertion direction B and positioning the tip 101 of the male connector 100 in the insertion direction B.

In the present embodiment, the tip receiving face 42 receives the tip curved face 101c of the male connector 100 via the elastic valve body 3; however, the tip receiving face 42 may receive the tip peripheral face 101a or the tip plane 101b instead of the tip curved face 101c of the male connector 100 or in addition to the tip curved face 101c. Moreover, in the present embodiment, the tip receiving face 42 receives the tip 101 of the male connector 100 via the elastic valve body 3; however, the tip receiving face 42 may receive the tip 101 by directly contacting one of the faces of the tip 101 of the male connector 100 without interposing the elastic valve body 3.

As illustrated in FIGS. 10 and 11, when the tip receiving face 42 receives the tip 101 of the male connector 100, the tip 101 of the male connector 100 and the upstream face 41 (liquid barrier face 39) of the partition section 40 are not in contact. That is, when the male connector 100 is received by the tip receiving face 42, the upstream face 41 (liquid barrier face 39) is positioned on the downstream side in the insertion direction B than the tip receiving face 42 so that the tip plane 101b of the male connector 100 does not contact with the upstream face 41 of the partition section 40. More specifically, the upstream face 41 of the present embodiment is a plane extending in the direction C perpendicular to the insertion direction B. The tip receiving face 42 is a curved face having, in the cross-sectional views in FIGS. 10 and 11, a linear cross section communicating with both ends of the upstream face 41 and having a predetermined angle in the direction C perpendicular to the insertion direction B.

That is, the tip receiving face 42 of the present embodiment includes two curved faces (linear lines in the cross-sectional views in FIGS. 10 and 11) opposite to each other in the direction C perpendicular to the insertion direction B. These two curved faces are formed in a tapered manner as illustrated in FIGS. 10 and 11 where the opposing distance in the direction C perpendicular to the insertion direction B decreases in the insertion direction B. An end of each of the two curved faces on the downstream side in the insertion direction B is communicated with the upstream face 41. Therefore, even when the tip receiving face 42 receives the tip 101 of the male connector 100, a space is formed between the tip plane 101b of the male connector 100 and the upstream face 41 (liquid barrier face 39) of the partition section 40 in the insertion direction B. The tip plane 101b of the male connector 100 therefore does not contact with the upstream face 41 of the partition section 40. Such a configuration prevents the upstream face 41 of the partition section 40 from blocking the tip opening 104 of the male connector 100 even when liquid such as liquid medicine is supplied from the tip opening 104 of the inserted male connector 100 into the connector 1. This allows for mitigating resistance of injection of liquid supplied from the male connector 100.

Next, a flow of liquid in the connector 1 will be described with reference to FIG. 9 where liquid such as liquid medicine is supplied from the tip opening 104 of the male connector 100 into the connector 1 while the tip receiving face 42 receives the tip 101 of the male connector 100. In FIG. 9, the flow of liquid in the connector 1 is illustrated by arrows.

Liquid flowing out from the tip opening 104 of the male connector 100 enters the connection flow path 38 of the flow path 6 and first collides on the upstream face 41 of the partition section 40 (liquid barrier face 39) as described above. The liquid collided on the upstream face 41 then proceeds along the upstream face 41 in the direction C perpendicular to the insertion direction B. In the present embodiment, the tip receiving face 42 is communicated with the upstream face 41 and the tip receiving face 42 receives the tip 101 of the male connector 100. Therefore, the liquid proceeding along the upstream face 41 flows toward the first connection flow path 43 and the second connection flow path 44 in the direction C perpendicular to the insertion direction B. Thereafter, the liquid passes through the first connection flow path 43 and the second connection flow path 44 and then flows into the tubular flow path 37.

The liquid flowing along the upstream face 41 toward the first connection flow path 43 and the second connection flow path 44 is pushed out with a rush from the outer edge of the upstream face 41 to the outside of the upstream face 41 in the direction C perpendicular to the insertion direction B. The liquid pushed out from the upstream face 41 thus reaches the opposite inner walls of the holder 8 (inner walls defining the connection flow path 38) interposing the first connection flow path 43, the second connection flow path 44, and the partition section 40 in the direction C perpendicular to the insertion direction B and forms a flow along these inner walls. As illustrated by the arrows in FIG. 9, the liquid having reached the inner walls defining the connection flow path 38 is bifurcated into a flow that enters into a space formed between the elastic valve body 3 and the housing 2 (see FIG. 2, etc.), specifically, the holder 8 and the inner wall of the bottom face cap 10 along these inner walls, and a flow that flows toward the first connection flow path 43 and the second connection flow path 44 along these inner walls. Most of the liquid flows into the tubular flow path 37 according to the latter flow.

As described above, the elastic valve body 3 is elastically deformed by the inserted male connector 100, enters between the inner wall of the bottom face cap 10 and the outer wall of the male connector 100, and is tightly attached to the outer face of the male connector 100. However, for example with an object of mitigating resistance of insertion of the male connector inserted from the outside, there are cases where a wide space capable of accommodating an elastic valve body is ensured between an inner wall of a housing such as a bottom face cap 10 and an outer wall of a male connector. In this case, although restoring force of the elastic valve body allows the elastic valve body to be tightly attached to the outer wall of the male connector, the elastic valve body may not be tightly attached to the inner wall of the housing. Other than the object of mitigating resistance of insertion, the elastic valve body may not be tightly attached to the inner wall of the housing due to attachment accuracy of the elastic valve body or dimensional tolerances of members included in the connector, for example. In such a case, liquid flowing out from the tip opening of the male connector where the male connector is inserted may enter a space formed at the aforementioned portion without tight attachment and continuously stagnate thereat. Furthermore, depending on a type of the liquid, continuous stagnation may result in of microbial growth.

Therefore in the present embodiment, as described above, the flow of liquid to follow the inner wall defining the connection flow path 38 is formed and, even if there is a space between the outer wall of the elastic valve body 3 and the inner walls of the holder 8 and the bottom face cap 10, the liquid is intentionally caused to enter the space. The liquid entering the space between the outer wall of the elastic valve body 3 and the inner walls of the holder 8 and the bottom face cap 10, for example, pushes, out of the space, liquid having entered the space to the connection flow path 38. This replaces liquid in the space, thereby suppressing continuous stagnation of the liquid in the space. The liquid having entered the space may be pushed out to the connection flow path 38 again from a position where the liquid have entered the space or a vicinity thereof; however, for example as illustrated in FIGS. 10 and 11, the liquid may pass through a tubular space surrounded by the tip receiving face 42, the elastic valve body 3, the holder 8, and the bottom face cap 10 to move in a circumferential direction having the insertion direction B in the center and is pushed out from a position different from the position where the liquid have entered the space or the vicinity thereof.

In this manner, the connector 1 of the present embodiment includes the partition section 40 including the upstream face 41 as the liquid barrier face 39 and thus is capable of suppressing generation of a turbulence flow of liquid in the flow path 6 and continuous stagnation of the liquid in the housing 2 (see FIG. 2, etc.).

[Infusion Set 110 Including Connector 1]

Figure 12:
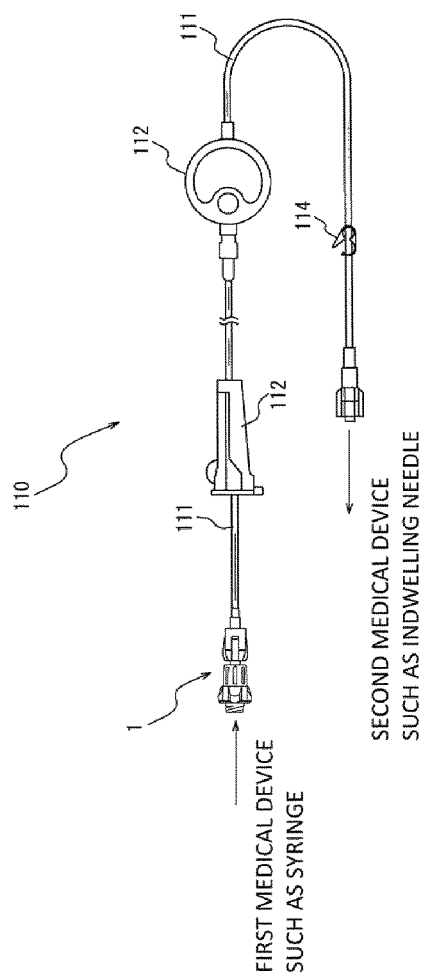
FIG. 12 is a diagram illustrating an infusion set as an embodiment of the present invention.

Lastly, an infusion set 110 including the connector 1 as an embodiment of the present invention will be described. FIG. 12 is a diagram illustrating the infusion set 110.

The infusion set 110 forms an infusion line connecting from a first medical device, such as a syringe, having the male connector 100 to a second medical device such as an indwelling needle. Specifically, the infusion set 110 of the present embodiment includes connector 1 to which the first medical device having a male connector such as a syringe is connected, a plurality of infusion solution tubes 111, a roller clamp 112 which adjusts a flow rate of liquid such as an infusion solution inside the infusion solution tube 111, an air vent filter 113 which discharges (or supplies) air present in the infusion line, and a clamp 114 which blocks the infusion solution tube 111.

In the present embodiment, the connector 1 is included at the position connecting the male connector with the first medical device; however, the position of the connector 1 is not limited thereto. For example regarding the infusion line as illustrated in FIG. 12 as a main line, a sub-line capable of mixture injection of other liquid medicine may be provided to the main line where the connector 1 may be provided to the sub-line as a mixture injection port.

Furthermore, the infusion set 110 of the present embodiment includes the connector 1, the infusion solution tubes 111, the roller clamp 112, the air vent filter 113, and the clamp 114; however, members to configure the infusion set is not limited thereto and may be changed as appropriate according to an object or usage of the infusion set such as further including a drip infusion cylinder or a T-shaped connector for mixture injection in addition to the above members.

The present invention is not limited to the configurations specified in the above embodiments but may include various modifications within a scope not departing from the principals of the invention described in the claims.

The term "top face cap" used herein refers to the cap in contact with the top face of the elastic valve body. Likewise, the term "bottom face cap" refers to the cap in contact with the bottom face of the elastic valve body.

INDUSTRIAL APPLICABILITY

The present disclosure relates to a connector and an infusion set. In particular, the disclosure invention relates to a connector that is capable of connecting thereto a male connector and an infusion set using the connector.

REFERENCE NUMERAL LIST 1 connector
2 housing
3 elastic valve body
4 hollow section
5 insertion section
6 flow path
7 cap
8 holder
9 top face cap
10 bottom face cap
11 slit
12 top face of elastic valve body
13 top face central region
14 top face outer region
15 top face annular groove
16 side wall
17 bottom face of elastic valve body
18 bottom face central region
19 thick region
20 bottom face outer region
21 bottom face annular groove
22 hollow barrel of top face cap
23 flange of top face cap
24 edge
25 screw thread
26 locking projection of top face cap 27 inner wall
28 extending section
29 hollow barrel of bottom face cap
30 flange of bottom face cap
31 locking projection of bottom face cap
32 clamping section
33 screw thread
34 outer barrel
35 male luer section
36 connection section
37 tubular flow path
38 connection flow path
39 liquid barrier face
40 partition section
41 upstream face of partition section
42 tip receiving face
43 first connection flow path
44 second connection flow path
45 downstream face of partition section
46 side face of partition section
50 side face of elastic valve body
60 partition section
61 upstream face
62 apex
63 side face
64 inclined face
65 downstream face
66 apex
67 inclined face
68 step face
70 partition member
71 support section
71a first fitting section
71b second fitting section
72 side face
73 cut-away section
73a upstream side cut-away section
73b downstream side cut-away section
74 upstream face
75 downstream face
76 step face
77 tip receiving face
78 step face
80 projecting wall section
81 upstream face
82 side face
83 downstream face
84 planar section
85 rib-shaped projection
86 step face
87 diameter expansion face
90 annular flange
91 upstream face
92 planar section
93 annular rib
100 male connector
101 tip
101a tip peripheral face
101b tip flat face
101c tip curved face
103 flow path of male connector
104 tip opening
110 infusion set
111 infusion solution tube
112 roller clamp
113 air vent filter
114 clamp
1000 connector
600 flow path
3800 connection flow path
B insertion direction of male connector
C direction perpendicular to insertion direction of male connector
D removal direction of male connector
E circumferential direction around the central axis of tubular flow path
O central axis of tubular flow path
W1 width of partition section interposed between flow paths
W2 width of inner wall defining connection flow path

The invention claimed is:

1. A connector comprising:
a housing comprising:
an insertion section into which a male connector is insertable from an outside of the housing,
an inner wall defining a flow path that communicates with the insertion section,
an inclined tip receiving face configured to receive a tip of the male connector, and
a partition section having a liquid barrier face,
wherein the inner wall, the inclined tip receiving face, and the partition section are formed together as a single piece; and
an elastic valve body having a slit and configured to block the insertion section,
wherein the housing is configured such that, when the male connector is inserted in the insertion section, the liquid barrier face faces a tip opening of the male connector in an insertion direction of the male connector such that liquid flowing out from the tip opening collides with the liquid barrier face, and
wherein at least one connection flow path extends in the insertion direction (i) through the inclined tip receiving face, or (ii) at a location radially inward of the inclined tip receiving face.

2. The connector according to claim 1, wherein:
the partition section divides the flow path in a direction perpendicular to the insertion direction, and
the liquid barrier face comprises an upstream face which is a face of the partition section on an upstream side in the insertion direction.

3. The connector according to claim 2,
wherein the partition section divides the flow path into a plurality of separated flow paths in the direction perpendicular to the insertion direction.

4. The connector according to claim 2,
wherein the upstream face is in a plane extending in the direction perpendicular to the insertion direction.

5. The connector according to claim 2,
wherein the upstream face is an inclined face descending from the upstream side to the downstream side in the insertion direction.

6. The connector according to claim 2,
wherein the partition section has a substantially round outer shape when viewed from the insertion direction.

7. The connector according to claim 1, wherein:
the housing comprises a projecting wall section projecting inward from the inner wall, and
the liquid barrier face comprises an upstream face of the projecting wall section on an upstream side in the insertion direction.

8. The connector according to claim 3, wherein a maximum width of the partition section interposed between the flow paths is smaller than an internal diameter of the housing defining an insertion opening that is one end of the insertion section when the housing is viewed from the insertion direction.

9. The connector according to claim 1, wherein:
the liquid barrier face is positioned on a downstream side with respect to the tip receiving face in the insertion direction.

10. An infusion set comprising the connector according to claim 1.

11. The connector according to claim 1, wherein the at least one connection flow path comprises a first connection flow path that extends in the insertion direction through the inclined tip receiving face on a first side of the partition section, and a second connection flow path that extends in the insertion direction through the inclined tip receiving face on a second side of the partition section.

12. The connector according to claim 7, wherein the at least one connection flow path comprises a single connection flow path that is defined on a first side by the inner wall of the housing and on a second side by a side face of the projecting wall section.

13. The connector according to claim 12, wherein a center axis of the housing extends through the single connection flow path.

14. The connector according to claim 12, wherein the upstream face of the projecting wall section comprises a planar section extending in a direction perpendicular to the insertion direction, and a rib-shaped projection projecting from the planar section in a removal direction of the male connector.

* * * * *